(12) United States Patent
Stanislaus et al.

(10) Patent No.: US 9,328,046 B2
(45) Date of Patent: May 3, 2016

(54) METHOD FOR DIRECT AMMONOLYSIS OF POLYCARBONATE-CONTAINING MATERIALS AND PRODUCTS

(71) Applicant: SAUDI BASIC INDUSTRIES CORPORATION, Riyadh (SA)

(72) Inventors: Alexander Stanislaus, Bangalore (IN); Venkata Ramanarayanan Ganapathy Bhotla, Bangalore (IN); P S Sreenivasan, Bangalore (IN); Philip Wesley Bell, Mount Vernon, IN (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 75 days.

(21) Appl. No.: 14/053,954

(22) Filed: Oct. 15, 2013

(65) Prior Publication Data

US 2015/0105531 A1    Apr. 16, 2015

(51) Int. Cl.
| | |
|---|---|
| *C08J 11/28* | (2006.01) |
| *C07C 37/00* | (2006.01) |
| *C08G 64/38* | (2006.01) |
| *C08J 11/16* | (2006.01) |

(52) U.S. Cl.
CPC ............. *C07C 37/00* (2013.01); *C08G 64/38* (2013.01); *C08J 11/16* (2013.01); *C08J 2369/00* (2013.01); *Y02W 30/705* (2015.05)

(58) Field of Classification Search
CPC ......... C07C 37/00; C08G 64/38; C08J 11/16; C08J 2369/00; Y02W 30/705
USPC ................................... 521/40–49.8
See application file for complete search history.

(56) References Cited

U.S. PATENT DOCUMENTS

| | | | |
|---|---|---|---|
| 4,605,762 A | 8/1986 | Mandoki | |
| 4,885,407 A | 12/1989 | Fox et al. | |
| 5,336,814 A | 8/1994 | Shafer | |
| 5,386,055 A | 1/1995 | Lee et al. | |
| 5,391,802 A | 2/1995 | Buysch et al. | |
| 5,675,044 A | 10/1997 | Eijsbouts et al. | |
| 7,585,930 B2 * | 9/2009 | Kitahara et al. | ............. 528/196 |
| 8,293,934 B2 | 10/2012 | Shinohata et al. | |
| 2004/0054238 A1 | 3/2004 | Ban et al. | |
| 2004/0127720 A1 | 7/2004 | Hedrick et al. | |
| 2004/0127744 A1 | 7/2004 | Hedrick et al. | |
| 2009/0215949 A1 * | 8/2009 | Fujiguchi et al. | ............. 524/430 |

FOREIGN PATENT DOCUMENTS

WO        9109004 A1    6/1991

OTHER PUBLICATIONS

Arai et al.; "Reactin kinetics of hydrothermal depolymerization of poly(ethylene naphthalate), poly(ethylene terephthalate), and polycarbonate with aqueous ammonia solution"; Chemical Engineering Science 65; pp. 36-41; 2010.

(Continued)

*Primary Examiner* — Frances Tischler
(74) *Attorney, Agent, or Firm* — Cantor Colburn LLP

(57) ABSTRACT

A method for recovering a dihydroxy aromatic compound and urea from a polycarbonate-containing composition comprising a polycarbonate and a phosphorus-containing flame retardant, comprising contacting the composition with ammonia in the presence of a swelling solvent for a time sufficient to depolymerize the polycarbonate producing a dihydroxy aromatic compound and urea.

19 Claims, 3 Drawing Sheets

Ammonia and methanol added together

(56) References Cited

OTHER PUBLICATIONS

Chang et al.; "Amination of polycarbonate surface and its application for cell attachment"; Artificial cells, blood subtitutes, and immobilization biotechnology; 27 (3); 229-44; May 1999; 22 pages.

CN 101407450 A; English Abstract; Date of Publication Apr. 15, 2009; 2 pages.

CN 101429100 A; English Abstract; Date of Publication May 13, 2009; 2 pages.

DE 10065087 A1; Derwent Record; Date of Publication Aug. 1, 2002; 2 pages.

Gaines, Jr., "Acceleration of Hydrolysis of Bisphenol a Polycarbonate by Hindered Amines"; Polymer Degradation and Stability, 27; 1990; pp. 13-18.

Hata et al.; "Chemical conversino of poly(carbonate) to 1.3-dimethyl-2-imidazolidinone (DMI) and bisphenol A: a practical approach to the chemical recycling of plastic wastes"; Polymer 43; pp. 2109-2116; 2002.

Machine Translation of JP 2001270961 A1; Date of Publication Oct. 2, 2001; 22 pages.

Machine Translation of JP 2001302844 A1; Date of Publication Oct. 31, 2001; 12 pages.

Machine Translation of JP 2002212335 A; Date of Publication Jul. 31, 2002; 12 pages.

Machine Translation of JP 2003231774 A; Date of Publication Aug. 19, 2003; 13 pages.

Machine Translation of JP 2004051620 A; Date of Publication Feb. 19, 2004; 45 pages.

Machine Translation of JP 2004323373 A; Date of Publication Nov. 18, 2004; 15 pages.

Machine Translation of JP 2004339340 A; Date of Publication Dec. 2, 2004; 14 pages.

Machine Translation of JP 2004339389 A; Date of Publication Dec. 2, 2004; 16 pages.

Machine Translation of JP 2005162674 A; Date of Publication Jun. 23, 2005; 17 pages.

Machine Translation of JP 2005162675 A; Date of Publication Jun. 23, 2005; 23 pages.

JP 2009184938 A; English Abstract; Date of Publication Aug. 20, 2009; 1 page.

Machine Translation of JP 2009184938 A; Date of Publication Aug. 20, 2009; 17 pages.

Machine Translation of JP2001302573 A; Date of Publication Oct. 31, 2001; 15 pages.

Machine Translation of JP 2004323374 A; Date of Publication Nov. 18, 2004; 3 pages.

Mormann et al.; "Ammonolysis of Polycarbonates with (Supercritical) Ammonia: An alternative for Chemical Recycling"; American Chemical Society; Chapter 18; pp. 244-261; 2005.

WO 2005026245 A1 English Abstract; Date of Publication Mar. 24, 2005; 2 pages.

Patent Cooperation Treaty, International Searching Authority, International Search Report, PCT/US2014/060450, Date of mailing: Dec. 12, 2014, 5 pages.

Patent Cooperation Treaty, International Searching Authority, Written Opinion, PCT/US2014/060450, Date of mailing: Dec. 12, 2014, 4 pages.

\* cited by examiner

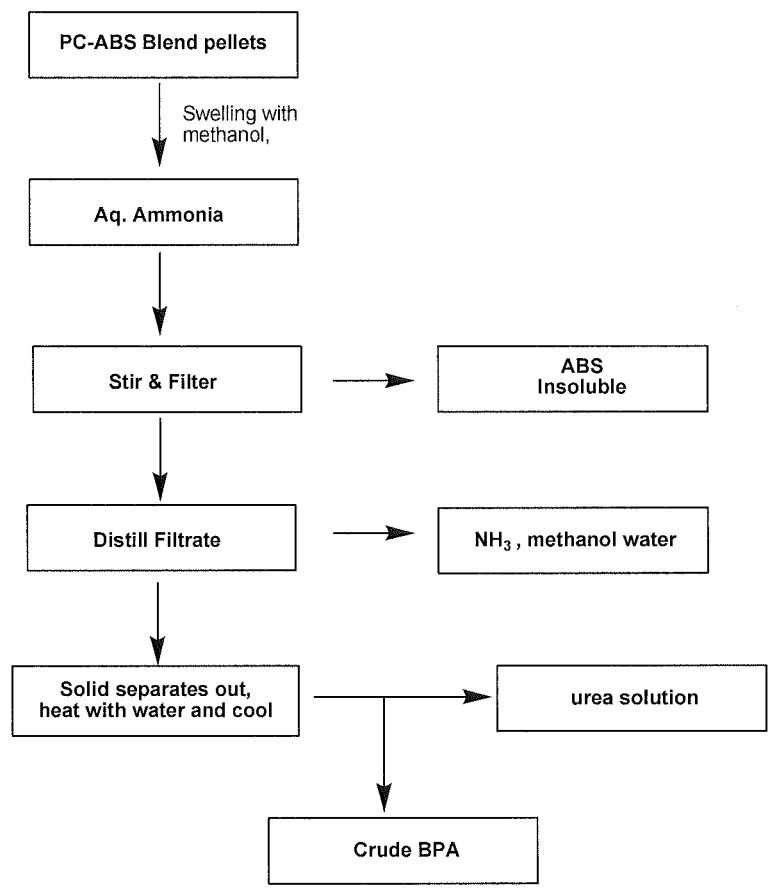
Fig. 1 Ammonia added after swelling with methanol

Fig. 2 Direct reaction with ammonia.
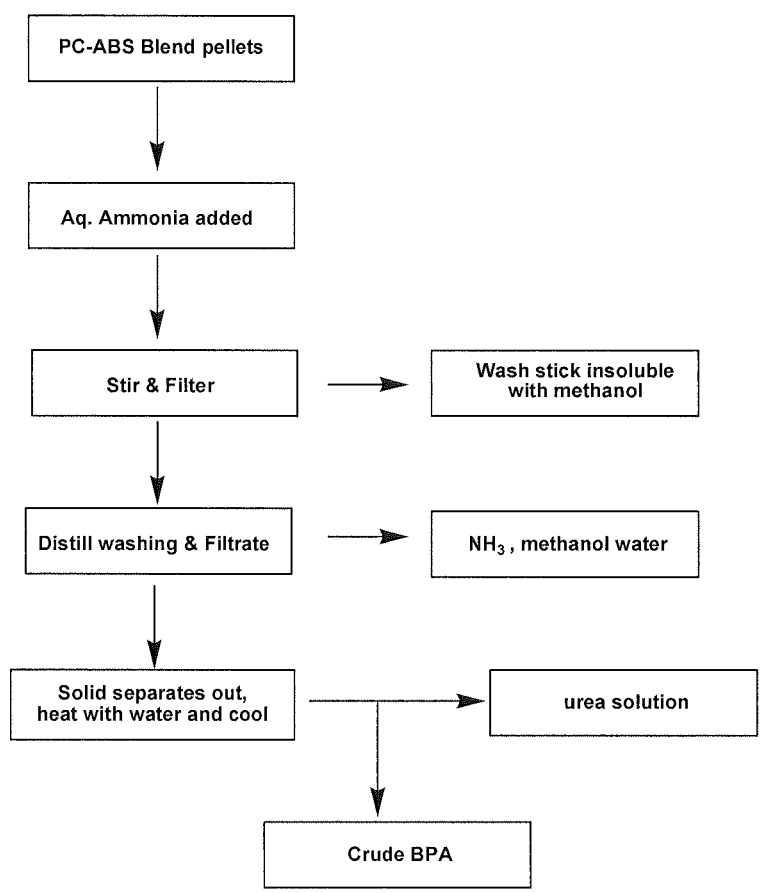

Fig. 3 Ammonia and methanol added together
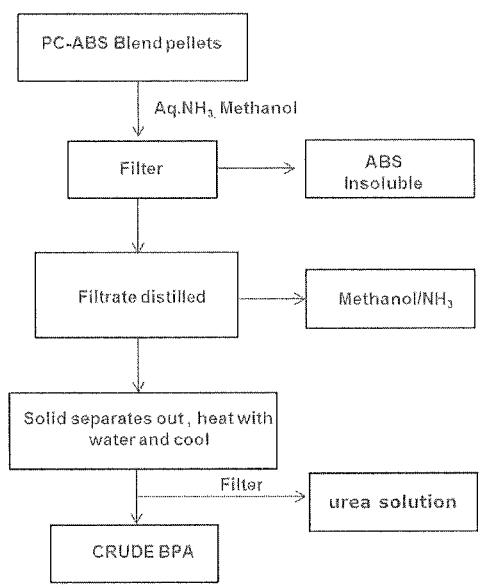

METHOD FOR DIRECT AMMONOLYSIS OF POLYCARBONATE-CONTAINING MATERIALS AND PRODUCTS

BACKGROUND

Plastics such as polyesters and polycarbonates have been widely employed, and chemical recycling of these compounds has become increasingly important. In response to customer demands and increasing governmental regulations, leading producers of engineered polymers such as acrylonitrile-butadiene-styrene (ABS), polycarbonate (PC), and PC blends are moving heavily into post-consumer plastics recycling.

Recycling processes can be classified into four major categories a) re-extrusion-primary, b) mechanical-secondary, c) chemical-tertiary, and d) energy recovery-quaternary. Each method provides a unique set of advantages that make it particularly beneficial for specific locations, applications, or requirements. Mechanical recycling (i.e., secondary or material recycling) involves physical treatment, while energy recovery involves complete or partial oxidation of the material producing heat, power, and/or gaseous fuels, oils, and chars. Chemical recycling or depolymerization on the other hand produces chemicals for the chemical industry. Depending upon the chemical agent used to break down the polymer, different depolymerization routes can be envisaged: glycolysis, methanolysis, hydrolysis, ammonolysis, etc.

It would be highly advantageous to have a low-cost source of chemically recycled post-consumer polycarbonate with good properties. The disadvantages of using traditional post-consumer recycle streams, such as water bottle regrinds and ground compact discs, are high cost, cumbersome multi-step process schemes, stability of source/quality of scrap waste, additives present in the recycle plastic, and chemical degradation resulting in inferior product properties.

SUMMARY OF THE INVENTION

Various illustrative embodiments are set forth herein, and are not to be viewed as limiting the scope of the invention.

Methods are provided for the ammonolysis of polycarbonate compositions containing flame retardants or acrylonitrile-butadiene-styrene, and in particular, methods of making bisphenol A by ammonolysis of bisphenol A polycarbonate compositions containing phosphorus-containing flame retardants or acrylonitrile-butadiene-styrene.

A method is disclosed for recovering a dihydroxy aromatic compound from a polycarbonate-containing composition comprising simultaneously contacting the polycarbonate-containing composition with ammonia and a solvent and maintaining at a temperature of from 20° C. to 100° C. for a time sufficient to depolymerize the polycarbonate to provide a dihydroxy aromatic compound and urea.

A method is disclosed for recovering a dihydroxy aromatic compound from a plastic composition comprising from 10 weight percent to 90 weight percent of a polycarbonate, the method comprising contacting the polycarbonate-containing composition with ammonia and a swelling solvent during substantially coextensive periods for a time sufficient to depolymerize the polycarbonate to provide a dihydroxy aromatic compound and urea.

A method is disclosed for recovering a dihydroxy aromatic compound from a plastic composition comprising from 10 weight percent to 90 weight percent of a polycarbonate, the method comprising contacting the polycarbonate-containing composition with a swelling solvent for period of from 1 to 10 hours, then contacting the polycarbonate-containing composition with ammonia for a time sufficient to depolymerize the polycarbonate and provide a dihydroxy aromatic compound and urea.

A method for recovering a dihydroxy aromatic compound from a polycarbonate-containing composition comprising a polycarbonate and a component comprising a phosphorus-containing flame retardant, or acrylonitrile-butadiene-styrene, or a combination of the phosphorus-containing flame retardant and acrylonitrile-butadiene-styrene, the method comprising contacting the polycarbonate-containing composition with ammonia for a time sufficient to depolymerize the polycarbonate to provide a dihydroxy aromatic compound and urea in a liquid phase and a solid residual polymeric composition having dihydroxy aromatic compound adhering to its surface, separating the solid residual polymeric composition from the liquid phase, and washing the solid polymeric composition with a suitable solvent, such as methanol, to recover additional dihydroxy aromatic compound.

In another embodiment, a process is provided that contacts the polycarbonate with ammonia and a suitable solvent, such as methanol, during substantially overlapping periods. As used herein, the term substantially overlapping periods means that two time periods run concurrently for a portion of their respective durations.

Another embodiment provides a process that contacts the polycarbonate with ammonia and a suitable solvent, such as methanol, during substantially coextensive periods. As used herein the term "substantially coextensive periods" means that two time periods run concurrently for a major portion of the duration of each time period, however the beginning and ending of each may, but need not, occur together.

Another embodiment provides a process that contacts the polycarbonate with ammonia and a suitable solvent, such as methanol, in a single step.

In another embodiment, a process is provided that contacts the polycarbonate with ammonia for a period of time sufficient to break the ester bonds and recovers the dialkyl carbonate by washing the residual solids with a suitable solvent, such as methanol.

In any of the preceding embodiments, the composition contains 10 to 90 weight percent polycarbonate, 10 to 70 weight percent polycarbonate, 20 to 50 weight percent polycarbonate, or 12 to 30 weight percent polycarbonate.

In any of the preceding embodiments, the solvent is a $C_{1-10}$ alcohol or a ketone, preferably the solvent is methanol.

In any of the preceding embodiments the method further comprises separating a blend of the alcohol and the urea from the dihydroxy aromatic compound by distillation.

In any of the preceding embodiments, the polycarbonate is bisphenol A polycarbonate, and the dihydroxy aromatic compound is bisphenol-A.

In any of the preceding embodiments, the phosphorus-containing flame retardant is bisphenol A bis(diphenyl phosphate), resorcinol bis(diphenyl phosphate), or a combination thereof.

In any of the preceding embodiments, further comprising recovering the dihydroxy aromatic compound generated, and polymerizing the dihydroxy aromatic compound and a carbonyl source to provide the polycarbonate. Another embodiment provides the polycarbonate so manufactured.

In some embodiments, the urea is isolated. In other embodiments, the urea is reacted to form $CO_2$ and $NH_3$. In a further embodiment, the $NH_3$ is reused in the process. In any of the preceding embodiments, the $CO_2$ is reacted with the dihydroxy aromatic compound to make a polycarbonate.

In any of the preceding embodiments, the dihydroxy aromatic compound is further processed to reduce the color thereof, for example, by solvent recrystallization or exposure to adsorbent or chelants to bind impurities.

BRIEF DESCRIPTION OF THE DRAWINGS

FIG. 1 illustrates the ammonolysis of a polycarbonate-ABS blend according to the reaction in Method-1.

FIG. 2 illustrates the ammonolysis of polycarbonate-ABS blend according to the reaction in Method-2.

FIG. 3 illustrates the ammonolysis of polycarbonate-ABS blend according to the reaction in Method-3.

DETAILED DESCRIPTION

The current invention establishes a non-catalytic method for carrying out ammonolysis of polycarbonate-containing plastic, such as electronic-waste, that also contains acrylonitrile-butadiene-styrene (ABS), and/or a phosphorus-containing flame retardant, such as bisphenol A bis(diphenyl phosphate) (BPADP) and other polymers such as polystyrene (PS), high-impact polystyrene (HIPS), polyurethane (PU), and the like. In an embodiment, the method is conducted under mild conditions, as further set out herein. When PC-containing electronic waste is subjected to direct ammonolysis, it allows for complete selective depolymerization of the PC component, even from materials that contain BPADP and/or ABS. Additionally, it is surprising to observe that under the reaction conditions the polymers in the recycled plastic other than PC remain intact, with the result that the bulk of these pellets/flakes retain a physical appearance similar to the starting material. This ability to carry out the ammonolysis of the PC-containing material and retain the physical appearance of the non-polycarbonate polymers enables a particularly efficacious route for recycling of low-value PC-containing materials.

A process is provided that surprisingly allows the separation and recovery of bisphenol A and urea from recycled plastics of low polycarbonate content, such as electronic wastes (E-wastes). The ammonia solution is of sufficient strength to selectively sever the ester bond of the polycarbonate and to form the ammonium salt of bisphenol-A (ammonium phenolate) which is soluble in the aqueous phase. A two phase system is formed, namely a solid phase and a liquid phase of which the liquid phase contains both urea and the ammonium salt of bisphenol-A. Separation of the phases is achieved by filtration.

The solid phase contains other materials such as fillers, pigments, reinforcing agents, other polymeric materials such as acrylonitrile-butadiene-styrene (ABS), polybutylene terephthalate (PBT), and the like.

From the liquid phase, the low boiling methanol and excess ammonia are distilled off This leaves urea dissolved in water and partially separated bisphenol-A by precipitation. Sufficient water is added until the bisphenol-A is precipitated out of the solution and removed by filtration. The solid bisphenol-A is then dried, may be purified and ready for use as an intermediate in chemical reactions.

In any of the preceding embodiments, the method further comprises separating the dihydroxy aromatic compound and the urea from the solid residual polymeric composition by filtration. The process severs the ester bond of bisphenol A-containing polyester such as a polycarbonate, a copolyester carbonate, a polyarylate, and the like, under mild conditions in a commercially feasible period of time.

Ammonia has a unique combination of solvent properties. The dipole moment of ammonia (1.65 Debye) is only slightly lower than that of water or methanol (1.8 and 1.65 Debye). The dielectric constant of ammonia (16.9) is one fifth that of water and even lower than that of ethanol. Like water, ammonia can act as both a hydrogen bond acceptor and donor. As a result, ammonia can dissolve a number of inorganic salts (e.g., halides, cyanides, thiocyanates, nitrates, or nitrites). Even more remarkable is that ammonia is miscible with water as well as polar organic compounds (alcohols, amines, esters) on one side and on the non-polar end with hydrocarbons like cyclohexane. Reactions which are heterogeneous in other solvents can be run under homogeneous conditions in ammonia.

Polycarbonates in E-waste polycarbonate compositions can be depolymerized by ammonolysis. As used herein, ammonolysis refers to a process that depolymerizes polycarbonate in the presence of ammonia to produce urea and bisphenol A, or depending on the particular polycarbonate composition, other dihydric phenols, or other dihydroxy aromatic compounds.

Swelling of the polymer particles in the method described herein is essentially free of dissolving the particles and increases the free volume of the particles. For example, alcohol does not dissolve a dihydric phenol such as that present in polycarbonate. The process for swelling of the polymer and the ammonolysis of the carbonate bonds can take place in several embodiments: in one step, by adding a suitable solvent, such as methanol, and ammonia together; sequentially, typically by swelling the particles and then adding the ammonia, although the ammonia can be added first to break bonds accessible at or near the surface and then swelling to reach bonds deeper within the plastic particles. These processes can be simultaneous or may overlap to a greater or lesser extent. The term "substantially coextensive" is intended to include embodiments where the swelling solvent and the ammonia are both present during the majority of the process interval, but does not require simultaneous addition, nor does it require that both remain present in significant quantities over the entire interval. In an embodiment, the ammonia breaks down the polycarbonate, however a significant portion of the resulting dihydroxy aromatic compound remains on the undissolved particles of non-polycarbonate plastics. In this embodiment, washing the non-polycarbonate plastic particles with a suitable solvent, such as methanol, yields a more complete recovery of the dihydroxy aromatic compound.

The recovered dihydric phenol, disclosed above, may be subjected to further purification by such means as distillation, recrystallization in a solvent, vacuum distillation, activated charcoal adsorption, or other purification processes.

In practice, the aqueous liquid phase contains dissolved urea which can then be recovered from the aqueous solution thereof Alternatively, the recovered urea can be purified or separated into its component parts, namely ammonia and carbon dioxide both of which or the urea itself have commercial use in the chemical industry.

Granulating the thermoplastic articles to a particular size is not critical to the ammonolysis. However, average particle size of the granulated material can be about 0.2 to about 10 millimeters (mm) in order to provide greater surface area exposure to the organic swelling solvent and ammonia. Generally, finer granulation increases the accessibility of reactive sites within the recycled plastic. The preferred size of the particles during granulation of the thermoplastic material can also be a function of the composition.

The organic swelling solvent may be any organic swelling solvent that is miscible with water and can be distilled off from an aqueous solution. Preferably, the organic swelling solvent is an alcohol. The alcohol can be any alcohol that will swell the thermoplastic particles and is preferably an alcohol of $C_1$-$C_{10}$ carbon, with the preferred alcohol being methanol. Other alcohols included herein are ethanol, propanol, isopropanol, butanol, and the like, including other organic alcohols. In addition, the other preferred organic swelling solvent is any ketone, but is preferably acetone, methyl ethyl ketone, isopropyl ketone, and the like.

Sufficient aqueous ammonia solution is added in order to selectively sever the ester bonds of the dihydric phenol units in, preferably, a relatively short period of time. The strength of the aqueous ammonia solution, i.e., ammonium hydroxide, is generally concentrated ammonium hydroxide. A saturated aqueous solution generally contains about 35% ammonia by mass, or 308 grams of ammonia per liter of water, and has a molarity of about 18. In an embodiment, a concentrated aqueous solution containing 20% to 30% ammonia by mass is employed. In another embodiment, the molarity of the ammonia solution ranges from 5 to 18. However, with lower concentrations of ammonia solution, longer contact times may be required for a desired yield of dihydric phenol. A suitable molar range of ammonium hydroxide to thermoplastic polymer can be 4.0 to 25 times and more particularly about 5 to about 25 times. It should be understood, however, that higher and lower molarity ammonium hydroxide can also be employed. In this process step, two phases are formed, a solid phase and a liquid phase.

The solid phase is then separated from the liquid phase. The liquid phase contains urea, water, the swelling solvent, and the ammonium salt of bisphenol-A (a dihydric phenolate ammonium salt). This liquid phase is then distilled to remove the swelling solvent and excess ammonia. Upon distillation of ammonia, the ammonium salt of bisphenol-A (BPA) transfers or converts to BPA. This leaves an aqueous solution of urea and partially precipitated bisphenol-A. Sufficient water is then added to the aqueous solution to maximize the precipitation of bisphenol-A. Separation of the two phases is accomplished by simple filtration. The solid bisphenol-A is dried and is usually in powder form. The recovered bisphenol-A may be purified and is available for use as a reactant in chemical reactions particularly for producing aromatic polycarbonates, epoxies, polyarylates, and such other products in which bisphenol-A is a reactant.

The polymeric materials that can be employed in the recovery process are those polymeric materials which are prepared using as one of the reactants, a dihydric phenol to form a polymer including, but not limited to, an aromatic polycarbonate as further described below, an aromatic copolyester carbonate, a polyarylate, or a combination thereof with other materials and/or polymers. Such other materials may include polymers such as polyamides (nylon), polyesters such as polybutylene terephthalate and polyethylene terephthalate, polyarylene ethers such as polyphenylene ether, and impact modifiers such as acrylonitrile-butadiene-styrene (ABS) and methyl methacrylate-butadiene-styrene (MBS), and the like. Other materials include fillers (glass, carbon, mineral, etc.), pigments, rubbers (natural or synthetic), reinforcing agents other than fillers, etc. These materials are separable from the polymer containing the dihydric phenol residue units in this process.

The ammonolysis of polycarbonate is generally conducted at a temperature of at least room temperature, more preferably 20° C., 30° C., 40° C., 50° C., 60° C., 70° C., 80° C., 90° C., 100° C., or at any higher temperature and pressure combination below the decomposition of the desired products, preferably a temperature from 50° C. to 200° C., more preferably 60° C. to 180° C. At temperatures below 30° C., reaction rates may become too slow for practical economical operation. Atmospheric, subatmospheric, or supra-atmospheric pressures can be used, for example from room pressure up to 40 bar, preferably from 50 mbar to 40 bar, more preferably from 5 bar to 20 bar pressure.

Urea and the swelling solvent recovered from the process can be separated and reused separately as for example the swelling solvent can be used in further polycarbonate swelling steps, or together, for example to produce dimethyl carbonate in the case where the swelling solvent is methanol.

The terms "room temperature" and "room pressure" as used in the specification and in the appended claims mean the conditions of temperature and pressure prevailing in the ambient in which a given determination is made or process step(s) is conducted, i.e., there is no application or withdrawal of heat from the designated material or process step different from that occurring in the ambient. Ordinarily, room temperature is in the range of about 20° C. and room pressure is atmospheric.

The ammonolysis of polycarbonate can be conducted for about 0.5 to about 24 hours, preferably about 1 to about 16 hours, more preferably about 4 to about 12 hours depending on the temperature and pressure and the specific polycarbonate-containing composition. Advantageously, the conversion of the polycarbonate is 99% complete in less than 10 hours.

As used herein, a "polycarbonate" means compositions having repeating structural carbonate units of formula (1)

(1)

in which at least 60 percent of the total number of $R^1$ groups contain aromatic moieties and the balance thereof are aliphatic, alicyclic, or aromatic. In an embodiment, each $R^1$ is a $C_{6-30}$ aromatic group, that is, contains at least one aromatic moiety. $R^1$ can be derived from a dihydroxy compound of the formula HO—$R^1$—OH, in particular of formula (2)

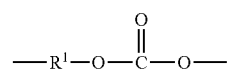

(2)

wherein each of $A^1$ and $A^2$ is a monocyclic divalent aromatic group and $Y^1$ is a single bond or a bridging group having one or more atoms that separate $A^1$ from $A^2$. In an embodiment, one atom separates $A^1$ from $A^2$. Preferably, each $R^1$ can be derived from a dihydroxy aromatic compound of formula (3)

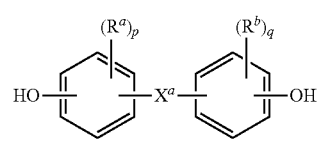

(3)

wherein $R^a$ and $R^b$ are each independently a halogen, $C_{1-12}$ alkoxy, or $C_{1-12}$ alkyl; and p and q are each independently integers of 0 to 4. It will be understood that $R^a$ is hydrogen when p is 0, and likewise $R^b$ is hydrogen when q is 0. Also in formula (3), $X^a$ is a bridging group connecting the two hydroxy-substituted aromatic groups, where the bridging group and the hydroxy substituent of each $C_6$ arylene group are disposed ortho, meta, or para (preferably para) to each other on the $C_6$ arylene group. In an embodiment, the bridging group $X^a$ is single bond, —O—, —S—, —S(O)—, —S(O)$_2$—, —C(O)—, or a C$_{1-18}$ organic group. The C$_{1-18}$ organic bridging group can be cyclic or acyclic, aromatic or non-aromatic, and can further comprise heteroatoms such as halogens, oxygen, nitrogen, sulfur, silicon, or phosphorous. The C$_{1-18}$ organic group can be disposed such that the C$_6$ arylene groups connected thereto are each connected to a common alkylidene carbon or to different carbons of the C$_{1-18}$ organic bridging group. In an embodiment, p and q is each 1, and R$^a$ and R$^b$ are each a C$_{1-3}$ alkyl group, preferably methyl, disposed meta to the hydroxy group on each arylene group.

In an embodiment, X$^a$ is a substituted or unsubstituted C$_{3-18}$ cycloalkylidene, a C$_{1-25}$ alkylidene of formula —C(R$^c$)(R$^d$)— wherein R$^c$ and R$^d$ are each independently hydrogen, C$_{1-12}$ alkyl, C$_{1-12}$ cycloalkyl, C$_{7-12}$ arylalkyl, C$_{1-12}$ heteroalkyl, or cyclic C$_{7-12}$ heteroarylalkyl, or a group of the formula —C(=R$^e$)— wherein R$^e$ is a divalent C$_{1-12}$ hydrocarbon group. Groups of this type include methylene, cyclohexylmethylene, ethylidene, neopentylidene, and isopropylidene, as well as 2-[2.2.1]-bicycloheptylidene, cyclohexylidene, cyclopentylidene, cyclododecylidene, and adamantylidene.

In another embodiment, X$^a$ is a C$_{1-18}$ alkylene group, a C$_{3-18}$ cycloalkylene group, a fused C$_{6-18}$ cycloalkylene group, or a group of the formula —B$^1$-G-B$^2$— wherein B$^1$ and B$^2$ are the same or different C$_{1-6}$ alkylene group and G is a C$_{3-12}$ cycloalkylidene group or a C$_{6-16}$ arylene group. For example, X$^a$ can be a substituted C$_{3-18}$ cycloalkylidene of formula (4)

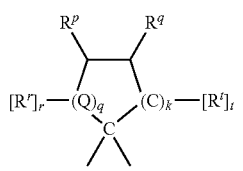

(4)

wherein R$^r$, R$^p$, R$^q$, and R$^t$ are each independently hydrogen, halogen, oxygen, or C$_{1-12}$ hydrocarbon groups; Q is a direct bond, a carbon, or a divalent oxygen, sulfur, or —N(Z)— wherein Z is hydrogen, halogen, hydroxy, C$_{1-12}$ alkyl, C$_{1-12}$ alkoxy, or C$_{1-12}$ acyl; r is 0 to 2, t is 1 or 2, q is 0 or 1, and k is 0 to 3, with the proviso that at least two of R$^r$, R$^p$, R$^q$, and R$^t$ taken together are a fused cycloaliphatic, aromatic, or heteroaromatic ring. It will be understood that where the fused ring is aromatic, the ring as shown in formula (4) will have an unsaturated carbon-carbon linkage where the ring is fused. When k is 1 and i is 0, the ring as shown in formula (4) contains 4 carbon atoms, when k is 2, the ring as shown in formula (4) contains 5 carbon atoms, and when k is 3, the ring contains 6 carbon atoms. In an embodiment, two adjacent groups (e.g., R$^q$ and R$^t$ taken together) form an aromatic group, and in another embodiment, R$^q$ and R$^t$ taken together form one aromatic group and R$^r$ and R$^p$ taken together form a second aromatic group. When R$^q$ and R$^t$ taken together form an aromatic group, R$^p$ can be a double-bonded oxygen atom, i.e., a ketone.

"Polycarbonates" includes homopolycarbonates (wherein each R$^1$ in the polymer is the same), copolymers comprising different R$^1$ moieties in the carbonate ("copolycarbonates"), copolymers comprising carbonate units, and other types of polymer units, such as ester units, and combinations comprising at least one of homopolycarbonates or copolycarbonates.

Polycarbonates containing flame retardants are also referred to as "FR polycarbonates" herein. FR polycarbonates are used in various components and housings in electronic devices. Once the devices are discarded, plastics are separated from metal and glass components and are processed to provide potential feedstocks for industrial use. These feedstocks are referred to as plastics from E-waste. Examples of FR polycarbonate-containing E-waste include plastics from float sink E-waste and trommel E-waste.

E-wastes of various types and grades contain various amounts of polycarbonate. The process provided can be used to recycle polycarbonate-containing materials, such as E-waste containing 3 to 99 weight percent polycarbonate; from 10 to 90 weight percent polycarbonate; 10 to 70 weight percent polycarbonate; from 10 to 50 weight percent polycarbonate; from 12 to 30 weight percent polycarbonate. The process provided can also be used to recycle virgin polycarbonate or plant rework batches having a content up to 100% polycarbonate.

E-waste materials can be first separated by hand prior to size reduction. Those parts that are believed to be primarily polycarbonate/ABS blends are hand-picked and used as recycling feedstocks. Such E-waste plastics are available from Recycletronics.

The phosphorus-containing flame retardants in the polycarbonate-containing compositions include organic phosphates and organic compounds containing phosphorus-nitrogen bonds.

One type of organic phosphate is an aromatic phosphate of the formula (GO)$_3$P=O, wherein each G is independently an alkyl, cycloalkyl, aryl, alkylaryl, or aralkyl group, provided that at least one G is an aromatic group. Two of the G groups can be joined together to provide a cyclic group, for example, diphenyl pentaerythritol diphosphite. Aromatic phosphates include, phenyl bis(dodecyl)phosphate, phenyl bis(neopentyl)phosphate, phenyl bis(3,5,5'-trimethylhexyl)phosphate, ethyl diphenyl phosphate, 2-ethylhexyl di(p-tolyl)phosphate, bis(2-ethylhexyl)p-tolyl phosphate, tritolyl phosphate, bis(2-ethylhexyl)phenyl phosphate, tri(nonylphenyl)phosphate, bis(dodecyl)p-tolyl phosphate, dibutyl phenyl phosphate, 2-chloroethyl diphenyl phosphate, p-tolyl bis(2,5,5'-trimethylhexyl)phosphate, 2-ethylhexyl diphenyl phosphate, or the like. A specific aromatic phosphate is one in which each G is aromatic, for example, triphenyl phosphate, tricresyl phosphate, isopropylated triphenyl phosphate, and the like.

Di- or polyfunctional aromatic phosphorus-containing compounds are also useful, for example, compounds of the formulae below:

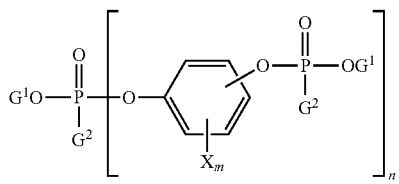

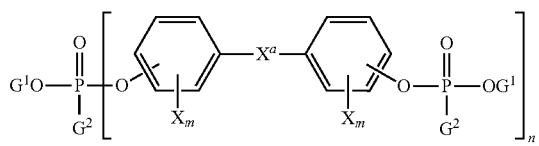

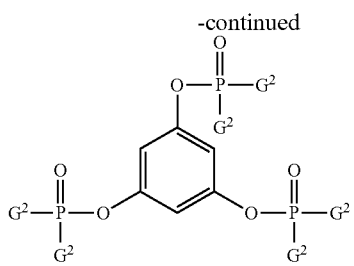

wherein each $G^1$ is independently a hydrocarbon having 1 to 30 carbon atoms; each $G^2$ is independently a hydrocarbon or hydrocarbonoxy having 1 to 30 carbon atoms; each X is independently a bromine or chlorine; m is 0 to 4, and n is 1 to 30. Di- or polyfunctional aromatic phosphorus-containing compounds include resorcinol tetraphenyl diphosphate (RDP), the bis(diphenyl)phosphate of hydroquinone and the bis(diphenyl)phosphate of bisphenol A, respectively, their oligomeric and polymeric counterparts, and the like.

Exemplary flame retardant compounds containing phosphorus-nitrogen bonds include phosphonitrilic chloride, phosphorus ester amides, phosphoric acid amides, phosphonic acid amides, phosphinic acid amides, and tris(aziridinyl) phosphine oxide. The organic phosphorus-containing flame retardants are generally present in amounts of about 0.1 to about 20 parts by weight, for example, about 2 to about 18 parts by weight or about 4 to about 16 parts by weight, optionally about 2 to about 15 parts by weight, based on 100 parts by weight of the total composition, exclusive of any filler.

The dihydroxy aromatic compound, such as BPA, obtained from this reaction can be sold as is or used in further reactions including polymerization to make polycarbonates, or as a feedstock to make phenol. The other plastics which remain in the pellets/flakes after processing can be sold or used as such for other applications, along with the urea byproduct recovered from the reaction.

For example, the dihydroxy aromatic compound can be used to form a polycarbonate by polymerization with a carbonyl source, i.e., a carbonate precursor. Polymerization of the dihydroxy aromatic compound to produce a polycarbonate can follow interfacial or melt polymerization methods. Although the reaction conditions for interfacial polymerization can vary, the process generally involves dissolving or dispersing a dihydroxy aromatic compound in aqueous caustic soda or potash, adding the resulting mixture to a water-immiscible solvent medium, and contacting the reactants with a carbonate precursor in the presence of a catalyst such as triethylamine or a phase transfer catalyst, under controlled pH conditions, e.g., 8 to 12. The most commonly used water immiscible solvents include methylene chloride, 1,2-dichloroethane, chlorobenzene, toluene, and the like.

Carbonate precursors include a carbonyl halide such as carbonyl bromide or carbonyl chloride, or a haloformate such as a bishaloformates of a dihydric phenol (e.g., the bischloroformates of bisphenol A, hydroquinone, or the like) or a glycol (e.g., the bishaloformate of ethylene glycol, neopentyl glycol, polyethylene glycol, or the like). Combinations comprising at least one of the foregoing types of carbonate precursors can also be used. In an embodiment, an interfacial polymerization reaction to form carbonate linkages uses phosgene as a carbonate precursor, and is referred to as a phosgenation reaction.

Among the phase transfer catalysts that can be used are catalysts of the formula $(R^3)_4Q^+X$, wherein each $R^3$ is the same or different, and is a $C_{1-10}$ alkyl group; Q is a nitrogen or phosphorus atom; and X is a halogen atom or a $C_{1-8}$ alkoxy group or $C_{6-18}$ aryloxy group. Phase transfer catalysts include, for example, $[CH_3(CH_2)_3]_4NX$, $[CH_3(CH_2)_3]_4PX$, $[CH_3(CH_2)_5]_4NX$, $[CH_3(CH_2)_6]_4NX$, $[CH_3(CH_2)_4]_4NX$, $CH_3[CH_3(CH_2)_3]_3NX$, and $CH_3[CH_3(CH_2)_2]_3NX$, wherein X is $Cl^-$, $Br^-$, a $C_{1-8}$ alkoxy group or a $C_{6-18}$ aryloxy group. An effective amount of a phase transfer catalyst can be 0.1 to 10 wt. % based on the weight of bisphenol in the phosgenation mixture. In another embodiment, an effective amount of phase transfer catalyst can be 0.5 to 2 wt. % based on the weight of bisphenol in the phosgenation mixture.

Branched polycarbonate blocks can be prepared by adding a branching agent during polymerization. A chain stopper (also referred to as a capping agent) can be included during polymerization. The chain stopper limits molecular weight growth rate, and so controls molecular weight in the polycarbonate.

Alternatively, melt processes can be used to make the polycarbonates. Melt polymerization may be conducted as a batch process or as a continuous process. In either case, the melt polymerization conditions used may comprise two or more distinct reaction stages, for example, a first reaction stage in which the starting dihydroxy aromatic compound and diaryl carbonate are converted into an oligomeric polycarbonate and a second reaction stage wherein the oligomeric polycarbonate formed in the first reaction stage is converted to high molecular weight polycarbonate. Such "staged" polymerization reaction conditions are especially suitable for use in continuous polymerization systems wherein the starting monomers are oligomerized in a first reaction vessel and the oligomeric polycarbonate formed therein is continuously transferred to one or more downstream reactors in which the oligomeric polycarbonate is converted to high molecular weight polycarbonate. Typically, in the oligomerization stage the oligomeric polycarbonate produced has a number average molecular weight of about 1,000 to about 7,500 Daltons. In one or more subsequent polymerization stages, the number average molecular weight (Mn) of the polycarbonate is increased to between about 8,000 and about 25,000 Daltons (using polycarbonate standard).

The term "melt polymerization conditions" is understood to mean those conditions necessary to effect reaction between a dihydroxy aromatic compound and a diaryl carbonate in the presence of a transesterification catalyst. Typically, solvents are not used in the process, and the reactants dihydroxy aromatic compound and the diaryl carbonate are in a molten state. The reaction temperature can be about 100° C. to about 350° C., preferably about 180° C. to about 310° C. The pressure may be at atmospheric pressure, supra-atmospheric pressure, or a range of pressures from atmospheric pressure to about 15 torr in the initial stages of the reaction, and at a reduced pressure at later stages, for example about 0.2 to about 15 torr. The reaction time is generally about 0.1 hours to about 10 hours.

Catalysts used in the melt transesterification polymerization production of polycarbonates can include alpha or beta catalysts. Beta catalysts are typically volatile and degrade at elevated temperatures. Beta catalysts are therefore preferred for use at early low-temperature polymerization stages. Alpha catalysts are typically more thermally stable and less volatile than beta catalysts.

The alpha catalyst can comprise a source of alkali or alkaline earth ions. The sources of these ions include alkali metal hydroxides such as lithium hydroxide, sodium hydroxide, and potassium hydroxide, as well as alkaline earth hydroxides such as magnesium hydroxide and calcium hydroxide. Other possible sources of alkali and alkaline earth metal ions include the corresponding salts of carboxylic acids (such as sodium acetate) and derivatives of ethylene diamine tetraacetic acid (EDTA) (such as EDTA tetrasodium salt, and EDTA magnesium disodium salt). Other alpha transesterification catalysts include alkali or alkaline earth metal salts of a non-volatile inorganic acid such as $NaH_2PO_3$, $NaH_2PO_4$, $Na_2HPO_3$, $KH_2PO_4$, $CsH_2PO_4$, $Cs_2HPO_4$, and the like, or mixed salts of phosphoric acid, such as $NaKHPO_4$, $CsNaHPO_4$, $CsKHPO_4$, and the like. Combinations comprising at least one of any of the foregoing catalysts can be used.

Possible beta catalysts can comprise a quaternary ammonium compound, a quaternary phosphonium compound, or a combination comprising at least one of the foregoing. The quaternary ammonium compound can be a compound of the structure $(R^4)_4N^+X^-$, wherein each $R^4$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Examples of organic quaternary ammonium compounds include tetramethyl ammonium hydroxide, tetrabutyl ammonium hydroxide, tetramethyl ammonium acetate, tetramethyl ammonium formate, tetrabutyl ammonium acetate, and combinations comprising at least one of the foregoing. Tetramethyl ammonium hydroxide is often used. The quaternary phosphonium compound can be a compound of the structure $(R^5)_4P^+C^-$, wherein each $R^5$ is the same or different, and is a $C_{1-20}$ alkyl group, a $C_{4-20}$ cycloalkyl group, or a $C_{4-20}$ aryl group; and $X^-$ is an organic or inorganic anion, for example a hydroxide, halide, carboxylate, sulfonate, sulfate, formate, carbonate, or bicarbonate. Where $X^-$ is a polyvalent anion such as carbonate or sulfate, it is understood that the positive and negative charges in the quaternary ammonium and phosphonium structures are properly balanced. For example, where $R^{20}$-$R^{23}$ are each methyl groups and $X^-$ is carbonate, it is understood that $X^-$ represents $2(CO_3^{-2})$. Examples of organic quaternary phosphonium compounds include tetramethyl phosphonium hydroxide, tetramethyl phosphonium acetate, tetramethyl phosphonium formate, tetrabutyl phosphonium hydroxide, tetrabutyl phosphonium acetate (TBPA), tetraphenyl phosphonium acetate, tetraphenyl phosphonium phenoxide, and combinations comprising at least one of the foregoing. TBPA is often used.

The amount of alpha and beta catalyst used can be based upon the total number of moles of dihydroxy compound used in the polymerization reaction. When referring to the ratio of beta catalyst, for example, a phosphonium salt, to all dihydroxy compounds used in the polymerization reaction, it is convenient to refer to moles of phosphonium salt per mole of the dihydroxy compound, meaning the number of moles of phosphonium salt divided by the sum of the moles of each individual dihydroxy compound present in the reaction mixture. The alpha catalyst can be used in an amount sufficient to provide $1\times10^{-2}$ to $1\times10^{-8}$ moles, preferably, $1\times10^{-4}$ to $1\times10^{-7}$ moles of metal per mole of the dihydroxy compounds used. The amount of beta catalyst (e.g., organic ammonium or phosphonium salts) can be $1\times10^{-2}$ to $1\times10^{-5}$, preferably $1\times10^{-3}$ to $1\times10^{-4}$ moles per total mole of the dihydroxy compounds in the reaction mixture.

Branched polycarbonate blocks can be prepared by adding a branching agent during polymerization. These branching agents include polyfunctional organic compounds containing at least three functional groups selected from hydroxyl, carboxyl, carboxylic anhydride, haloformyl, and mixtures of the foregoing functional groups. Specific examples include trimellitic acid, trimellitic anhydride, trimellitic trichloride, tris-p-hydroxy phenyl ethane, isatin-bis-phenol, tris-phenol TC (1,3,5-tris((p-hydroxyphenyl)isopropyl)benzene), tris-phenol PA (4(4(1,1-bis(p-hydroxyphenyl)-ethyl) alpha, alpha-dimethyl benzyl)phenol), 4-chloroformyl phthalic anhydride, trimesic acid, and benzophenone tetracarboxylic acid. The branching agents can be added at a level of 0.05 to 2.0 weight %. Mixtures comprising linear polycarbonates and branched polycarbonates can be used.

The various embodiments are further illustrated by the following non-limiting examples.

EXAMPLES

Materials

PC-ABS blends such as CYCOLOY and Modified CYCOLAC were obtained from SABIC. Other commercial E-wastes were procured from different sources such as Recycletronics, ECS, E-world, and Synergy.

TABLE 1

| Component | Description | Source |
| --- | --- | --- |
| Sample #1 CYCOLOY | A polycarbonate feedstock containing about 70 wt. % of bisphenol A polycarbonate; about 17 wt. % of acrylonitrile-butadiene-styrene; and about 11 wt. % of bisphenol A bis(diphenyl phosphate). | SABIC |
| Sample # 2 (Recycle Grade-E-waste) | Polymer blends recovered from electronic devices containing about 70 wt. % of polycarbonates as determined by IR | Recycletronics |
| Sample # 3 (Recycle Grade-E-waste) | Polymer blends recovered from electronic devices containing about 30 wt. % of polycarbonates as determined by IR | E-world-White |
| Sample # 4 (Recycle Grade-E-waste) | Polymer blends recovered from electronic devices containing about 13 wt. % of polycarbonates as determined by IR | Synergy |
| Sample # 5 (Recycle Grade-E-waste) | Polymer blends recovered from electronic devices containing about 90 wt. % of polycarbonates as determined by IR | ECS |
| Sample # 6 Virgin modified CYCOLAC | Feedstock containing about 9% PC, 80% ABS, 11% BPADP | SABIC |
| Sample # 7 (Recycle Grade-E-waste) | Polymer blends recovered from electronic devices containing about 3.7 wt. % of polycarbonates as determined by IR | E-world-Black |
| Mill-Q water | Ultrapure water from Milli-Q lab water system | Millipore |
| Methanol | | Merck |

TABLE 1-continued

| Component | Description | Source |
|---|---|---|
| BPA | 2,2-Bis(4-hydroxyphenyl) propane | Ammonolysis product |
| Urea | | Ammonolysis product |

Procedures and Techniques
Polycarbonate Content of Materials by Infrared (IR) Analysis The PC content in the E-wastes was quantified by infrared analysis (IR). A quantity of the material was dissolved in dichloromethane (DCM). The solution was then filtered to remove insolubles. To the DCM solution, methanol was added to re-precipitate the polymer. The polymer was then recovered by filtration, dried and weighed. This sample was then dissolved in chloroform and quantified for PC by IR in a 0.5 cm pathlength $CaF_2$ liquid cell and the resulting compositional analysis was used to back calculate and find the PC content in the starting material.

Ammonolysis Procedures

Ammonolysis of the polycarbonate-containing polymer was conducted using three methods, described below.

Method-1

To about 30 grams (g) of CYCOLOY pellets (with 70% PC content), 125 milliliters (ml) of methanol was added. The resulting mixture was stirred at room temperature for a determined period of time to swell the pellets (initial duration was 2 hours). To this, 125 ml of 30% aqueous $NH_3$ was added and stirred at the indicated temperature. The reaction was stopped at the conclusion of the indicated time. The mixture was then filtered to remove the insolubles and the filtrate was distilled to remove ammonia, methanol, and most of the water, leaving the ammonium salt of BPA as a solid. The ammonium salt of BPA was then converted to BPA by treating with water, heating to 100° C. for an hour, and then cooling to room temperature. (Entries 1-8 in Table-2)

Method-2

To about 30 g of CYCOLOY pellets (with 70% PC content), 125 ml of 30% aqueous $NH_3$ was added and stirred at the indicated temperature. The reaction was stopped at the conclusion of the indicated time. The mixture was then filtered to remove the insolubles. The solid remaining on the filter was observed to be sticky and was then washed with methanol to remove additional soluble material. The methanol from the washing step was combined with the filtrate solution and then distilled to remove ammonia, methanol, and most of the water. Upon distillation, the ammonium salt of BPA was recovered as a solid. The ammonium salt of BPA was then converted to BPA by treating with water, heating to 100° C. for an hour, and then cooling to room temperature. The mixture was then filtered to separate the BPA from urea since urea is soluble in water while BPA has very low solubility. This demonstrates that when methanol was not used in the ammonolysis, some of the BPA product stuck to the insoluble ABS and did not come out in solution. A BPA yield of 71.3% and purity of 82% was obtained. It required a thorough methanol wash to free the BPA from the ABS. In contrast, the presence of methanol during the ammonolysis as in Method-1 kept the BPA product in solution.

Method-3

To about 30 g of CYCOLOY pellets (with 70% PC content), 125 ml of methanol and 125 ml of 30% aqueous $NH_3$ was added and stirred at the indicated temperature. The reaction was stopped after 6 or 9 hours. The mixture was then filtered to separate the insolubles and the filtrate was distilled to remove ammonia, methanol, and most of the water. Upon distillation, the ammonium salt of BPA was recovered as a solid. The ammonium salt of BPA was then converted to BPA by treating with water, heating to 100° C. for an hour, and then cooling to room temperature. The mixture was then filtered to separate the water-insoluble BPA from the water-soluble urea. (Entries 9-12 in Table-2 and entries 13-18 in Table-3)

Results and Discussion

Chemical recycling of plastics to monomers or to other appropriate starting materials for re-synthesis of polymers is the method of choice when these materials are contaminated with other polymers or inorganic materials or when they are part of a composite. A non-catalytic method for carrying out ammonolysis of a polycarbonate-containing blend and electronic-waste that also contains Acrylonitrile Butadiene Styrene (ABS), BPADP and/or other polymers such as PBT, PET etc. under mild conditions is provided.

Accessibility of ammonia to the carbonate moieties is the key for depolymerization. Therefore, swelling of the pellets was preferred so as to provide greater exposure of the carbonates to ammonia. The solvent chosen was such that it is miscible with water and could be distilled off from aqueous solutions. Methanol was chosen so that the product formed by depolymerization of PC, i.e., BPA and urea were in solution while the other polymer (mostly ABS) remained as insoluble polymer pellets or flakes.

Under the reaction conditions, the polymers other than polycarbonate appear to remain intact in that the bulk of the pellets/flakes retain the same physical appearance as the starting material. The ability to carry out the ammonolysis of the PC-containing material and retain the physical appearance of the insoluble polymers enables the efficient recycling of low-value PC-containing materials.

A series of reactions were conducted varying the swelling time from 2 hours to 6 hours and at temperatures ranging from room temperature to 70° C. The results are tabulated in Table 2.

TABLE 2

Details of ammonolysis reactions of CYCOLOY blend

| | Swelling | | Ammonolysis | | Total | Weight of | Weight of | | Weight of | % Yield of |
|---|---|---|---|---|---|---|---|---|---|---|
| Ex. # | Time (hrs) | Temp (° C.) | Time (hrs) | Temp (° C.) | Reaction Time (hrs) | insolubles (g) | Crude BPA (g) | % Purity of BPA | Recovered BPA (g) | BPA Recovered |
| 1 | 2 | RT | 6 | 40 | 8 | 8.5 | 10.6 | 94.8 | 10.0 | 64 |
| 2 | 6 | RT | 6 | 40 | 12 | 10.7 | 9.8 | 99.0 | 9.7 | 62 |

TABLE 2-continued

Details of ammonolysis reactions of CYCOLOY blend

| | Swelling | | Ammonolysis | | Total | Weight of | Weight of | | Weight of | % Yield of |
|---|---|---|---|---|---|---|---|---|---|---|
| Ex. # | Time (hrs) | Temp (° C.) | Time (hrs) | Temp (° C.) | Reaction Time (hrs) | insolubles (g) | Crude BPA (g) | % Purity of BPA | Recovered BPA (g) | BPA Recovered |
| 3 | 6 | RT | 18 | 40 | 24 | 7.2 | 13.3 | 96.9 | 12.9 | 82 |
| 4 | 3 | RT | 18 | 40 | 21 | 8.3 | 12.7 | 96.8 | 12.3 | 78 |
| 5 | 3 | 70 | 18 | 40 | 21 | 7.2 | 14.0 | 91.2 | 12.8 | 81 |
| 6 | 6 | 70 | 18 | 40 | 24 | 7.3 | 13.5 | 97.5 | 13.2 | 84 |
| 7 | 6 | 70 | 6 | 40 | 12 | 8.4 | 12.5 | 96.6 | 12.1 | 77 |
| 8 | 3 | 70 | 6 | 70 | 9 | 7.2 | 12.9 | 93.3 | 12.0 | 77 |
| 9 | 0 | NA | 6 | 70 | 6 | 10.2 | 11.4 | 96.3 | 11.0 | 70 |
| 10 | 0 | NA | 9 | 70 | 9 | 6.0 | 14.4 | 90.3 | 13.0 | 83 |
| 11 | 0 | NA | 9 | 50 | 9 | 8.0 | 12.8 | 94.6 | 12.1 | 77 |
| 12 | 0 | NA | 9 | 60 | 9 | 6.5 | 13.9 | 94.5 | 13.1 | 84 |

Swelling Time and Temperature—Example 1 was run with a swelling time of 2 hours at room temperature and produced 94.8% purity of BPA and a 64% yield. Increasing the swelling time in Example 2 from 2 hours to 6 hours improved purity but did not improve the yield significantly. In Examples 7 & 8, the swelling was carried out at 70° C. which increased the percent yield by 15%. In Example 8 the swelling time was reduced from the 6 hours of Example 7 to 3 hours and produced the same percentage yield as in Example 7 with only a slight reduction in BPA purity.

Ammonolysis Time—In Example 2, the ammonolysis time was 6 hours and increasing the ammonolysis time to 18 hours in Example 3 improved the yield by 20 percentage points, with a slight reduction in purity. Similar results were observed in Example 6 versus Example 7 where the longer ammonolysis time produced the better yield. In Example 6, the total reaction time including the swelling time was 24 hours for a maximum yield of 84%. Although this yield was quite acceptable, the total reaction time was longer than desirable for economic feasibility.

When the 18 hours of ammonolysis time employed above was reduced to 6 hours in Example 7, the percent yield was reduced by 7. When the swelling time was reduced to 3 hours in Example 8, a yield of 77% and purity of 93.3% was obtained with a total reaction time of 9 hours.

In Example 10, Method-3 was followed wherein the swelling time of 3 hours was integrated with ammonolysis time of 6 hours by heating the polymer with a 1:1 mixture of methanol and aqueous Ammonia for a total of 9 hours, 83% yield and 90% purity of BPA was obtained. In Example 9, reducing the total process time to 6 hours gave lesser yield.

Examples 10, 11, and 12 show surprisingly good purity and yield at temperatures from 50° C. to 70° C.

Once the method was optimized, ammonolysis of E-waste with varying PC content was carried out. The results were promising and are tabulated in Table 3.

TABLE 3

Details of Ammonolysis of Electronic wastes

| Ex. # | Sample (PC content) | Swelling Time | Ammonolysis Time | Ammonolysis Temp | Total Process (hrs) | Weight of insolubles (g) | Weight of Crude BPA (g) | % Purity BPA | Product Weight BPA (g) | % Yield BPA |
|---|---|---|---|---|---|---|---|---|---|---|
| 13 | Sample # 2 ~70% | 0 | 9 | 60 | 9 | 5.2 | 14.6 | 95.3 | 13.9 | 89 |
| 14 | Sample # 3 ~30% | 0 | 9 | 60 | 9 | 16.7 | 5.4 | 96.9 | 5.3 | 80 |
| 15 | Sample # 4 ~13.1% | 0 | 9 | 60 | 9 | 20.8 | 2.6 | 91.6 | 2.4 | 82 |
| 16 | Sample # 5 ~90% | 0 | 9 | 60 | 9 | 0.5 | 20.3 | 98.0 | 19.9 | 99 |
| 17 | Sample # 6 ~9% | 0 | 9 | 60 | 9 | 25.0 | NA | NA | NA | no reaction |
| 18 | Sample # 7 ~3.7% | 0 | 9 | 60 | 9 | 24.0 | NA | NA | NA | no reaction |

Examples 13, 14, and 15 produced yield above 80% in 9 hours from E-waste of 70%, 30%, and 13.1% Polycarbonate content. Example 16 processed a 90% PC content material to obtain 99% yield and 98% purity in 9 hours.

Example 17 was a reaction of virgin modified CYCOLAC with a composition containing 9% PC and 80% ABS and the remainder BPADP. Surprisingly there was no depolymerization observed and no yield of BPA. This could be due to the fact that the ammonia molecule finds it extremely difficult to reach the carbonate linkage of PC which is surrounded by the ABS. On the other hand, Example 15 was a reaction with E-waste with the overall PC content of only 13% but still depolymerization did take place. Although the E-waste had less PC content, unlike modified CYCOLOY it is heterogeneous. Some of the flakes may have a higher PC content while some may not contain PC. On the whole, the PC content is 13%. A more heterogeneous distribution of the polycarbonate within the E-waste may improve accessibility of the ammonia to the active carbonate sites within those E-waste particles having higher PC content, as opposed to the uniformly low PC content in the modified CYCOLOY. Also these E-wastes have been subjected to heat treatment during processing unlike the virgin material.

In Example 18, the reaction using E-waste with only 3% PC also did not give any BPA. Since the PC content is too low, accessibility to the carbonate linkage would be extremely difficult.

Treatment of BPA Obtained from Feedstock #3 to Improve APHA Value

The crude dihydroxy aromatic compound, such as bisphenol A, derived from ammonolysis of a polycarbonate-containing composition can have a color value on the American Public Health Association color index (referred to as "APHA values"). APHA is a single number yellowness index and is measured in accordance with ASTM D1209. A higher APHA value translates to a more yellow colored sample.

Method-1: Toluene Crystallization

To 10 grams of crude BPA with an APHA of 957, 80 ml of toluene was added and heated to 120° C. BPA dissolved in toluene at this temperature and a clear solution was obtained. After maintaining the temperature for 3 hours, it was cooled to room temperature. BPA crystallized out and was filtered and washed with cold toluene. The crystallized sample was dried and analyzed by HPLC for 97.2% purity. The APHA of the recrystallized sample was reduced to 346 (Table-4). The APHA was measured on a 70 weight percent (weight/volume) solution in methanol using a Macbeth color eye 7000A instrument. The APHA shift relative to the blank (methanol) is given as the APHA of the sample.

Method-2: Charcoal/Methanol/Water Precipitation 10 g of crude BPA was dissolved in 20 ml methanol and stirred at room temperature for 15 minutes. 500 mg of special grade activated charcoal was added and stirred for 30 minutes. It was then filtered. To the filtrate, Milli-Q water was added drop wise. Addition was stopped as soon as precipitation occurred. It was allowed to stir for another 15 minutes and filtered. The purified BPA was dried and (APHA) was measured to be 130. When toluene crystallized BPA (by Method-1) was treated by Method 2, the APHA improved to 97 by the ASTM D1209 method. On repeating Method 2 two times and four times the APHA value improved to 45 and 30 respectively.

Method-3: Two Charcoal Treatments Followed by Methanol/Water Treatment 10 g of crude BPA was dissolved in 20 ml methanol and stirred at room temperature for 15 minutes. 500 mg of special grade activated charcoal was added and stirred for 30 minutes. It was then filtered. 500 mg of fresh charcoal of the same grade was added to the filtrate and stirred for 30 minutes. It was then filtered. Milli-Q water was added drop wise to this filtrate. Addition was stopped as soon as precipitation occurred. It was allowed to stir for another 15 minutes and filtered. The purified BPA was dried and APHA was measured to be 116.

TABLE 4

APHA measurements of BPA from Feedstock # 3 at various stages

| Material | APHA |
| --- | --- |
| Standard Virgin-BPA | 17 |
| Crude BPA from Feedstock # 3 | 957 |
| Crude BPA from Feedstock # 3 treated by Method-2 | 130 |
| Crude BPA from Feedstock # 3 treated by Method-3 | 116 |
| Crude BPA from Feedstock # 3 treated by Method-1 | 346 |
| Toluene crystallized BPA treated by Method-2 once | 97 |
| Toluene crystallized BPA treated by Method-2 two times | 45 |
| Toluene crystallized BPA treated by Method-2 four times | 30 |

CONCLUSION

PC found in PC blends and commercial electronic wastes can be depolymerized in a simple and mild way using aqueous ammonia solution. BPA was obtained in good purity and yield. The crude BPA obtained can be purified by solvent crystallization to give higher purity and the color of BPA could be improved by charcoal treatment. An APHA value of 30 could be achieved after multiple methanol/water charcoal treatments.

The singular forms "a," "an," and "the" include plural referents unless the context clearly dictates otherwise. "Or" means "and/or." Thus, reference to "compositions containing flame retardant or ABS," for example, means composition containing flame retardant, ABS, or both. The endpoints of all ranges directed to the same component or property are inclusive and independently combinable. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

As used herein, a "combination" is inclusive of blends, mixtures, alloys, reaction products, and the like. Compounds are described using standard nomenclature. For example, any position not substituted by any indicated group is understood to have its valency filled by a bond as indicated, or a hydrogen atom. A dash ("—") that is not between two letters or symbols is used to indicate a point of attachment for a substituent. For example, —CHO is attached through carbon of the carbonyl group.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof; "alkyl" refers to a straight or branched chain, saturated monovalent hydrocarbon group; "alkylene" refers to a straight or branched chain, saturated, divalent hydrocarbon group; "alkylidene" refers to a straight or branched chain, saturated divalent hydrocarbon group, with both valences on a single common carbon atom; "alkenyl" refers to a straight or branched chain monovalent hydrocarbon group having at least two carbons joined by a carbon-carbon double bond; "cycloalkyl" refers to a non-aromatic monovalent monocyclic or multicylic hydrocarbon group having at least three carbon atoms, "cycloalkenyl" refers to a non-aromatic cyclic divalent hydrocarbon group having at least three carbon atoms, with at least one degree of unsaturation; "aryl" refers to an aromatic monovalent group containing only carbon in the aromatic ring or rings; "arylene" refers to an aromatic divalent group containing only carbon in the aromatic ring or rings; "alkylaryl" refers to an aryl group that has been substituted with an alkyl group as defined above, with 4-methylphenyl being an exemplary alkylaryl group; "arylalkyl" refers to an alkyl group that has been substituted with an aryl group as defined above, with benzyl being an exemplary arylalkyl group; "acyl" refers to an alkyl group as defined above with the indicated number of carbon atoms attached through a carbonyl carbon bridge (—C(=O)—); "alkoxy" refers to an alkyl group as defined above with the indicated number of carbon atoms attached through an oxygen bridge (—O—); and "aryloxy" refers to an aryl group as defined above with the indicated number of carbon atoms attached through an oxygen bridge (—O—).

Unless otherwise indicated, each of the foregoing groups can be unsubstituted or substituted, provided that the substitution does not significantly adversely affect synthesis, stability, or use of the compound. The term "substituted" as used herein means that at least one hydrogen on the designated atom or group is replaced with another group, provided that the designated atom's normal valence is not exceeded. When the substituent is oxo (i.e., =O), then two hydrogens on the atom are replaced. Combinations of substituents or variables are permissible provided that the substitutions do not significantly adversely affect synthesis or use of the compound. Exemplary groups that can be present on a "substituted" position include, but are not limited to, cyano; hydroxyl; nitro; azido; alkanoyl (such as a $C_{2-6}$ alkanoyl group such as acyl); carboxamido; $C_{1-6}$ or $C_{1-3}$ alkyl, cycloalkyl, alkenyl, and alkynyl (including groups having at least one unsaturated linkages and from 2 to 8, or 2 to 6 carbon atoms); $C_{1-6}$ or $C_{1-3}$ alkoxy groups; $C_{6-10}$ aryloxy such as phenoxy; $C_{1-6}$ alkylthio; $C_{1-6}$ or $C_{1-3}$ alkylsulfinyl; C1-6 or $C_{1-3}$ alkylsulfonyl; aminodi ($C_{1-6}$ or $C_{1-3}$)alkyl; $C_{6-12}$ aryl having at least one aromatic rings (e.g., phenyl, biphenyl, naphthyl, or the like, each ring either substituted or unsubstituted aromatic); $C_{7-19}$ alkylene-aryl having 1 to 3 separate or fused rings and from 6 to 18 ring carbon atoms, with benzyl being an exemplary arylalkyl group; or arylalkoxy having 1 to 3 separate or fused rings and from 6 to 18 ring carbon atoms, with benzyloxy being an exemplary arylalkoxy group.

All references cited herein are incorporated by reference in their entirety. While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

We claim:

1. A method for recovering a dihydroxy aromatic compound from a polycarbonate-containing composition comprising contacting the polycarbonate-containing composition with ammonia and a swelling solvent during substantially coextensive periods at a temperature of from 50° C. to 100° C. for a time sufficient to depolymerize the polycarbonate to provide a dihydroxy aromatic compound and urea and to obtain insoluble polymer, other than polycarbonate, that retains a physical appearance which enables its recycle.

2. The method of claim 1, wherein the composition comprises from 10 to 90 weight percent polycarbonate.

3. The method of claim 1, wherein the composition comprises from 10 to 70weight percent polycarbonate.

4. The method of claim 1, wherein the composition comprises from 20 to 50weight percent polycarbonate.

5. The method of claim 1, wherein the composition comprises from 12 to 30weight percent polycarbonate.

6. The method of claim 1, wherein the swelling solvent is a $C_{1-10}$alcohol or a ketone.

7. The method of claim 6, wherein the swelling solvent is methanol.

8. The method of claim 1, wherein the method further comprises separating the dihydroxy aromatic compound and the urea from the solid residual polymeric composition by filtration.

9. The method of claim 1, further comprising separating a blend of the swelling solvent and the urea from the dihydroxy aromatic compound by distillation.

10. The method of claim 1, wherein the polycarbonate is bisphenol A polycarbonate, and the dihydroxy aromatic compound is bisphenol-A.

11. The method of claim 1, wherein the polycarbonate-containing composition, in addition to comprising 10 to 90 weight percent polycarbonate, further comprises a phosphorus-containing flame retardant selected from the group consisting of bisphenol A bis(diphenyl phosphate), resorcinol bis(diphenyl phosphate), and a combination thereof.

12. The method of claim 1, wherein the urea is isolated.

13. The method of claim 1, wherein the urea obtained by the depolymerization of the polycarbonate is further reacted to form $CO_2$ and $NH_3$.

14. The method of claim 13, wherein the $NH_3$ is reused in the process.

15. The method of claim 1, wherein the dihydroxy aromatic compound obtained by the depolymerization of the polycarbonate is further processed to reduce the color thereof.

16. The method of claim 15, wherein the further processing is selected from the group of solvent recrystallization or exposure to adsorbent or chelants to bind impurities.

17. A method for recovering a dihydroxy aromatic compound from a polycarbonate-containing composition containing 10 weight percent to 90 weight percent of a polycarbonate, acrylonitrile-butadiene-styrene, and phosphorous-containing flame retardant, which method comprises contacting the composition with ammonia and, as a swelling solvent, which swelling agent comprises a $C_{1-10}$ alcohol or ketone, during substantially coextensive periods at a temperature of from 50° C. to 100° C. for a time sufficient to depolymerize the polycarbonate to provide a dihydroxy aromatic compound, urea, and insoluble acrylonitrile-butadiene-styrene as pellets or flakes that retain a physical appearance that enables their recycle, wherein the method further comprises separating the dihydroxy aromatic compound and the urea from the insoluble acrylonitrile-butadiene-styrene by filtration and then separating a blend of the alcohol or ketone and the urea from the dihydroxy aromatic compound by distillation.

18. The method of claim 17 wherein the polycarbonate-containing composition is electronic waste consisting of polycarbonate, acrylonitrile-butadiene-styrene, and phosphorous-containing flame retardant and wherein the polycarbonate content is 10 to 70 weight percent.

19. The method of claim 17 wherein the polycarbonate-containing composition has a polycarbonate content that is 10 to 50 weight percent.

* * * * *